US 8,052,730 B2

(12) United States Patent
Brown et al.

(10) Patent No.: US 8,052,730 B2
(45) Date of Patent: Nov. 8, 2011

(54) THERAPEUTIC DEVICE FOR THERMALLY ASSISTED URINARY FUNCTION

(76) Inventors: Mark Brown, Newtown, PA (US);
Daniel Higgins, Jamison, PA (US)

( * ) Notice: Subject to any disclaimer, the term of this patent is extended or adjusted under 35 U.S.C. 154(b) by 1047 days.

(21) Appl. No.: 11/919,466

(22) PCT Filed: Aug. 11, 2006

(86) PCT No.: PCT/US2006/031431
§ 371 (c)(1),
(2), (4) Date: Oct. 26, 2007

(87) PCT Pub. No.: WO2007/021967
PCT Pub. Date: Feb. 22, 2007

(65) Prior Publication Data
US 2009/0105793 A1    Apr. 23, 2009

Related U.S. Application Data

(60) Provisional application No. 60/707,716, filed on Aug. 12, 2005.

(51) Int. Cl.
*A61F 7/00* (2006.01)
*A61N 1/00* (2006.01)
(52) U.S. Cl. .......... 607/108; 607/96; 607/114; 607/143; 607/41; 602/70
(58) Field of Classification Search .................. 607/108, 607/143, 96, 114, 41; 2/78.3, 403; 62/269.3; 606/27–31
See application file for complete search history.

(56) References Cited

U.S. PATENT DOCUMENTS

| 734,213 | A | | 7/1903 | Barnes |
|---|---|---|---|---|
| 1,477,187 | A | * | 12/1923 | Rayne .............................. 602/71 |
| 3,680,563 | A | * | 8/1972 | Forrest .......................... 607/112 |
| 4,938,221 | A | | 7/1990 | Tuffel |
| 5,243,974 | A | | 9/1993 | Allen |
| 5,417,721 | A | | 5/1995 | Mallasch |
| 5,618,279 | A | * | 4/1997 | Pudlo ....................... 604/385.09 |
| 5,807,299 | A | | 9/1998 | McRoberts et al. |
| 6,061,840 | A | * | 5/2000 | Alligator ........................... 2/403 |
| 6,308,341 | B1 | | 10/2001 | Shelton |
| 6,648,909 | B2 | * | 11/2003 | Helming ....................... 607/108 |
| 6,862,746 | B2 | * | 3/2005 | Cym et al. ......................... 2/403 |

* cited by examiner

*Primary Examiner* — Linda Dvorak
*Assistant Examiner* — Adam Avigan
(74) *Attorney, Agent, or Firm* — Michael Crilly, Esq.

(57) ABSTRACT

A therapeutic device for thermally assisted urinary function is presented. The therapeutic pad (14) is composed of an upper thermal element (18) and a lower thermal element (19) having a portal (15), both elements substantially cup-shaped to cover and contact the groin. The therapeutic pad (14) is composed of a material sufficiently capable of storing energy from either an external or internal source. The therapeutic pad (14) communicates stored energy as heat to tissues comprising the groin and regions adjacent thereto. The portal (15) allows for the unimpeded flow of urine from the urinary tract into a receptacle. A variety of alternate embodiments are provided, including lift tabs (17a, 17b), an extension element (35) for heating the perineum, a portal sleeve (23) for heating the penis, a slit (34) which bisects the therapeutic pad (14) and portal sleeve (23), a pair of rings (26, 27) to open and close the slit (34), an interior cover (30) about the therapeutic pad (14) for applying moist heat, and support elements (31) along the therapeutic pad (14).

20 Claims, 15 Drawing Sheets

THERAPEUTIC DEVICE FOR THERMALLY ASSISTED URINARY FUNCTION

CROSS REFERENCE TO RELATED APPLICATIONS

This application is based upon and claims priority under 35 U.S.C. §119(e) from U.S. Provisional Application No. 60/707,716 filed Aug. 12, 2005 and PCT Application No. PCT/US06/31431 filed on Aug. 11, 2006, the contents of which are hereby incorporated in their entirety by reference thereto.

FEDERALLY SPONSORED RESEARCH AND DEVELOPMENT

None.

BACKGROUND OF THE INVENTION

1. Field of the Invention

The present invention relates to a device capable of initiating and enhancing urine flow from a bladder. Specifically, the invention is a therapeutic device that communicates thermal energy to the groin and penis in a non-invasive fashion, so as to enable vasodilation and neurological stimulation of the urinary track and to relax muscles in the surrounding tissue and bladder neck. The invention is contoured and conformal, thereby maximizing contact with the groin and transfer of heat thereto.

2. Description of the Related Art

Bladder and urinary tract dysfunctions are common among males over the age of forty. Dysfunction may be caused by several prostate-related medical conditions, including Benign Prostatic Hyperplasia, commonly referred to as BPH, Prostatitis, and Prostate Cancer. Benign Prostatic Hypertrohpy is defined as a benign, otherwise non-cancerous, adenomatous hyperplasia of the paraurethral prostate gland. Prostatitis is an inflammation of the prostate gland, usually due to an infection. Prostate cancer, as the name suggests, is a malignant growth involving the prostate.

As shown in FIG. 1, the prostate 1 is a doughnut-shaped gland with two lobes located at the bottom of the bladder 4 between the rectum 2 and base of the penis 3, adjacent to the scrotum 6. The prostate 1 encircles the urethra 5, the latter facilitating flow of urine from the bladder 4 out through the penis 3. An enlargement of the prostate 1 causes narrowing of the urethra 5, thereby diminishing urine flow in part or whole.

Symptoms of an enlarged prostate might include difficulty initiating urination, weak urine stream, persistent urge to urinate, and frequent nocturnal urination. In severe cases, obstruction of urine flow may lead to complications, including complete blockage of the urethra, urinary tract infections, stones in the bladder, and blood in the urine. It is estimated that at least seventy percent of men have noticeable enlargement of the prostate by the age of 70.

A variety of treatments, including medications and surgical procedures, are presently known to address the causes and/or symptoms of an enlarged prostate.

Medications are intended to control the growth of and in some cases shrink the prostate. For example, Finasteride limits the production of dihydrotestosterone (DHT), the hormone believed to control prostate growth. Side effects include reduced sex drive, erectile dysfunction, and decreased sperm count. In another example, alpha blockers relax the muscles of the bladder neck and prostate, producing a slight increase in urinary flow. Side effects include headaches, dizziness, light headedness, low blood pressure, fatigue and a sense of difficulty in breathing.

Medical procedures include transurethral resection of the prostate (TURP), transurethral incision of the prostate (TUIP), transurethral ultrasound guided laser incision of the prostate (TULIP), interstitial laser coagulation (ILC), transurethral vaporization of the prostate (TUVP), prostatic stent implantation, open prostatectomy, transurethral microwave thermotherapy (TUMT), Targis™, transurethral needle ablation of the prostate (TUNA), and water induced thermotherapy (WIT).

TURP is a procedure requiring anesthesia but no external incision. A resectoscope, having a light, valves to control irrigation fluid, and an electrical loop to cut then seal blood vessels, is inserted into the penis through the urethra. The loop is used to remove prostate tissue in pieces, which are then carried into the bladder via irrigating fluids, and flushed out after the procedure.

TUIP widens the urethra by making several small cuts along the neck of the bladder and prostate. This procedure reduces pressure applied by the prostate onto the urethra, thereby making urination easier. TULIP is identical to TUIP, except that cuts are made with a laser.

ILC requires the insertion of a cystoscope into the urethra to introduce a special fiberoptic probe directly into the prostate. The probe focuses a beam of low-power laser energy to vaporize prostate tissue so as to shrink the prostate.

TUVP is a transurethral procedure, which employs a grooved roller bar to directly apply heat to the prostate so as to vaporize tissue therein.

A prostatic stent implant is a tiny, spring-like device inserted into the urethra. When expanded, the stent widens the urethra to permit increased flow of urine. Prostatic stents are preferred for patients who have other medical problems that prohibit medication and surgery.

Open prostatectomy is preferred when the prostate is greatly enlarged, the bladder has been damaged, or the patient has other complications prohibiting transurethral surgery. The patient is anesthetized and an external incision is made either in the lower abdomen or in the perineum. Thereafter, prostate tissue is removed from inside the gland.

TUMT employs a catheter having an antenna at one end to deliver heat via microwave energy to the prostate in a targeted fashion. Deep heating of the prostate improves urine flow via a reduction in the size of the prostate. A fiberoptic thermosensor monitors temperature throughout the procedure and a cooling system circulates water within the catheter to protect the urinary tract.

Targis™ is an advanced form of microwave therapy, including a flexible catheter inserted into the urethra, for the targeted delivery of energy to destroy tissue in the prostate. A balloon at the end of the catheter is inflated to position the microwave antenna within the prostate. Chilled water is circulated through the catheter to shield healthy urethral tissue from thermal effects.

TUNA delivers low level radio frequency (RF) energy onto the prostate via two small probes inserted through the urethra. RF energy heats and shrinks the prostate, thereby relieving the obstruction while avoiding damage to the urethra and surrounding tissue.

WIT heats the prostate via a treatment balloon filled with heated water. The treatment balloon, resting in the prostatic urethra, inflates and then fills with water. Temperature controlled water then circulates through the insulated shaft into the treatment balloon. The catheter conducts heat through the insulated shaft to the prostate gland, raises the temperature of the gland, and then destroys the obstructive tissue.

The procedures described above are invasive in that one or more medical instruments are inserted into the body so as to heat, destroy, and/or remove tissue comprising the prostate. Furthermore, each procedure suffers from at least one post-procedure complication, including pain, frequent urination, swelling, bleeding, infection, sexual dysfunction, and prolonged recovery time.

The side effects of medications and complications associated with surgical procedures far outweigh the benefits to most males with prostate-related bladder and urinary tract dysfunction.

As such, what is sorely required is a therapeutic device to relieve the symptoms of prostate related urinary dysfunction while avoiding the side effects and complications of the related arts.

SUMMARY OF THE INVENTION

An object of the present invention is to provide a non-invasive, non-surgical, drugless therapeutic device capable of initiating urination via vaso-dilation, neurological stimulation, and warming of the urethra, prostate, urinary tract, and muscles adjacent thereto.

As represented in FIG. 2, the pudendal nerve 8 is formed from the sacral nerve roots S2, S3, and S4 from the backbone 13, which exit the pelvis to enter the gluteal region through the lower part of the greater sciatic foramen and reenter the pelvis through the lesser sciatic foramen. Thereafter, the pudendal nerve 8 gives rise to the inferior rectal nerve 9, perineal nerve 10, posterior scrotal nerves 11, and dorsal nerve 12 of the penis 3. In females, the dorsal nerve 12 terminates in the clitoris. The pudendal nerve 8 communicates sensations from the penis 3, scrotum 6, rectum 2, and perineum 7, all shown in FIG. 1, to the brain. The pudendal nerve 8 is understood to be responsible for urination in both males and females. Likewise, thermal stimulation of the pudendal nerve 8 is understood to induce urination directly or via the inferior rectal nerve 9, perineal nerve 10, posterior scrotal nerves 11, and/or dorsal nerve 12. The present invention is applied to the groin to thermally stimulate blood vessels, tissue, and nerves within and adjacent to the groin so as to initiate urination and to increase the stream and volume thereof.

The present invention is composed of a pad substantially shaped to cover and contact the groin and having a portal there through. The pad is composed of a material sufficiently capable of storing energy from either an external source or an internal source. The pad is capable of communicating this energy as heat to tissues comprising the groin and regions adjacent thereto. The portal is provided through the pad to allow for the passage of urine out of the urinary tract and to surround and stimulate the penis.

A variety of alternate embodiments are provided, including the following: at least one lift tab disposed along an edge of the pad for retrieval from a heating device; an extension pad attached to the pad at one end to facilitate heating of tissue adjacent to and behind the groin; a portal sleeve disposed about the portal and projecting outward from the pad for heating a penis passing through the pad; a slit bisecting the pad and portal sleeve to facilitate a further opening of the present invention for positioning about the penis; a pair of rings disposed about the slit so as to enable opening and closing of the slit for placement of the present invention about the penis and securing the present invention to the penis during use; an external cover about the pad capable of storing and communicating moisture to the groin; and support elements along the pad either externally or internally mounted thereto for the purpose of retaining the shape of the pad with or without adjustment.

The described invention provides several advantages over the related arts. The invention avoids the side effects associated with medications used to treat an enlarged prostate. The invention is non-invasive and non-surgical, thereby avoiding the complications associated with surgical procedures. The invention may be used to induce urination "on-the spot" for the purpose of collecting urine samples at a medical facility. The present invention facilitates the collection of urine samples under controlled conditions, thereby preventing sample substitution for the purpose of circumventing medical and drug screenings.

BRIEF DESCRIPTION OF DRAWINGS

Additional aspects, features, and advantages of the invention will be understood and will become more readily apparent when the invention is considered in the light of the following description made in conjunction with the accompanying drawings, wherein.

DETAILED DESCRIPTION OF THE INVENTION

Figure 1:
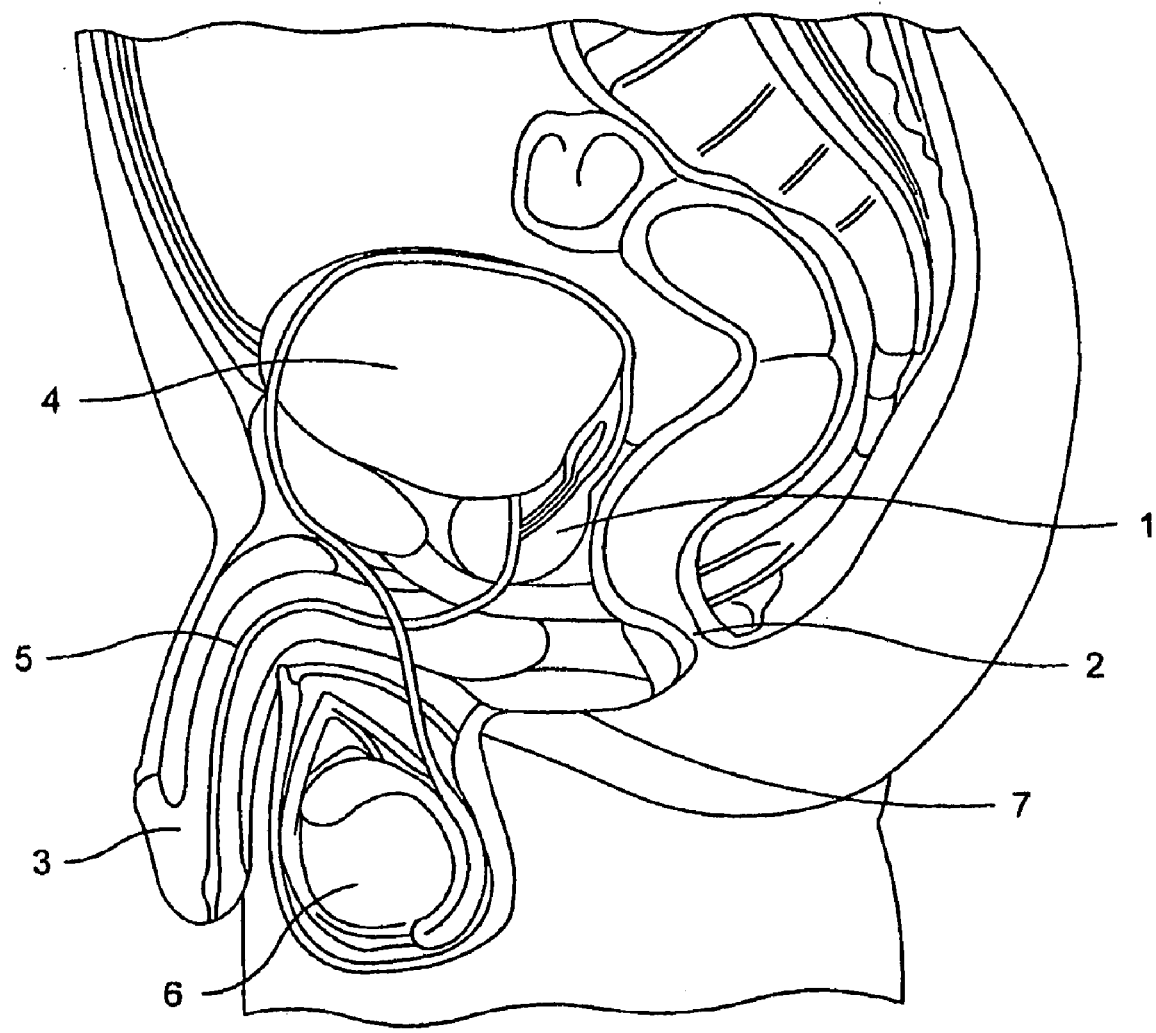
FIG. 1 is an anatomical diagram showing genitals, bladder, urinary tract, prostate, and rectum.
Figure 2:
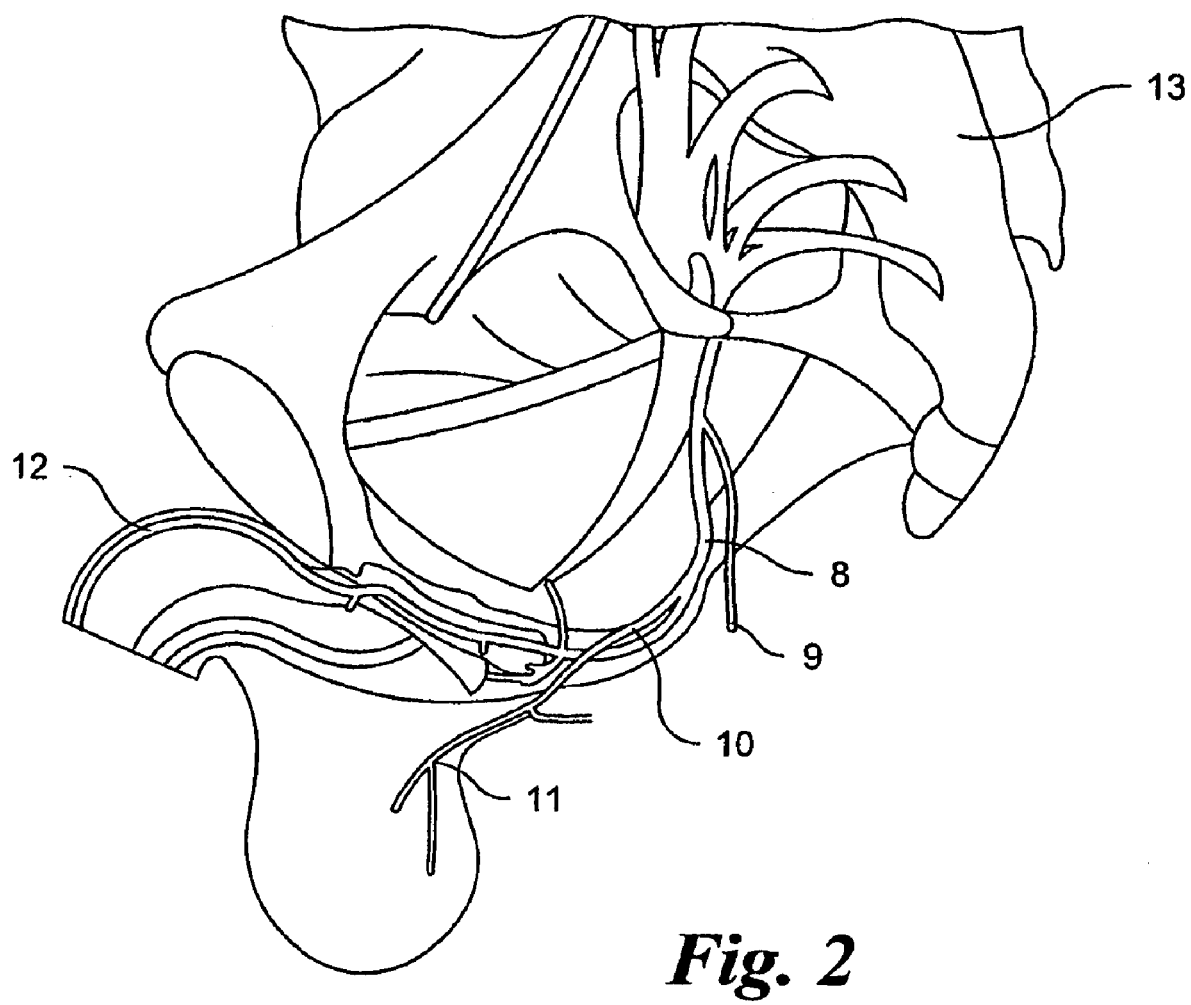
FIG. 2 is an anatomical diagram showing the nerve structure within a deep dissection of the gluteal region.
Figure 3A:
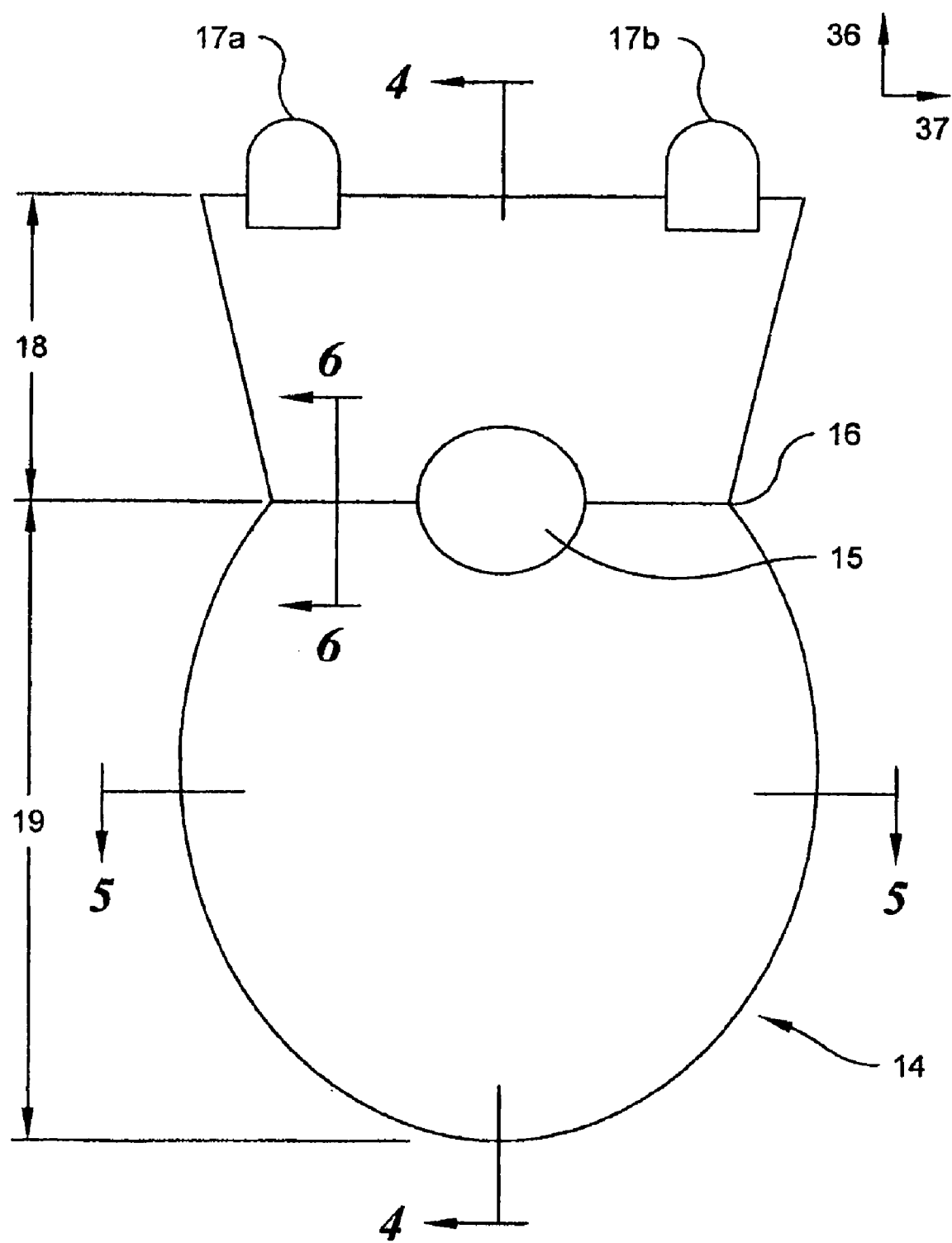
FIG. 3a is a frontal elevation view of the present invention showing upper and lower heating elements disposed about a portal.

Referring now to FIG. 3a, the present invention, herein referred to as a therapeutic pad 14, is a thermal device substantially shaped to cover and contact the groin region in a conformal fashion. Groin is understood to include the crease or hollow at the junction of the inner part of each thigh with the trunk together with tissues, nerves, and blood vessels within adjacent regions, and may also include genitals and portion of the abdominal wall. Upper and lower are for descriptive purposes and not intended to be limiting.

The therapeutic pad 14 is shown and described herein having a trapezoidal-shaped upper thermal element 18, an elliptical-shaped lower thermal element 19 and a substantially circular portal 15. Upper and lower thermal elements 18, 19 are composed of a thermally heatable material. The portal 15 is a hole completely traversing the thickness of the therapeutic pad 14.

Figure 3B:
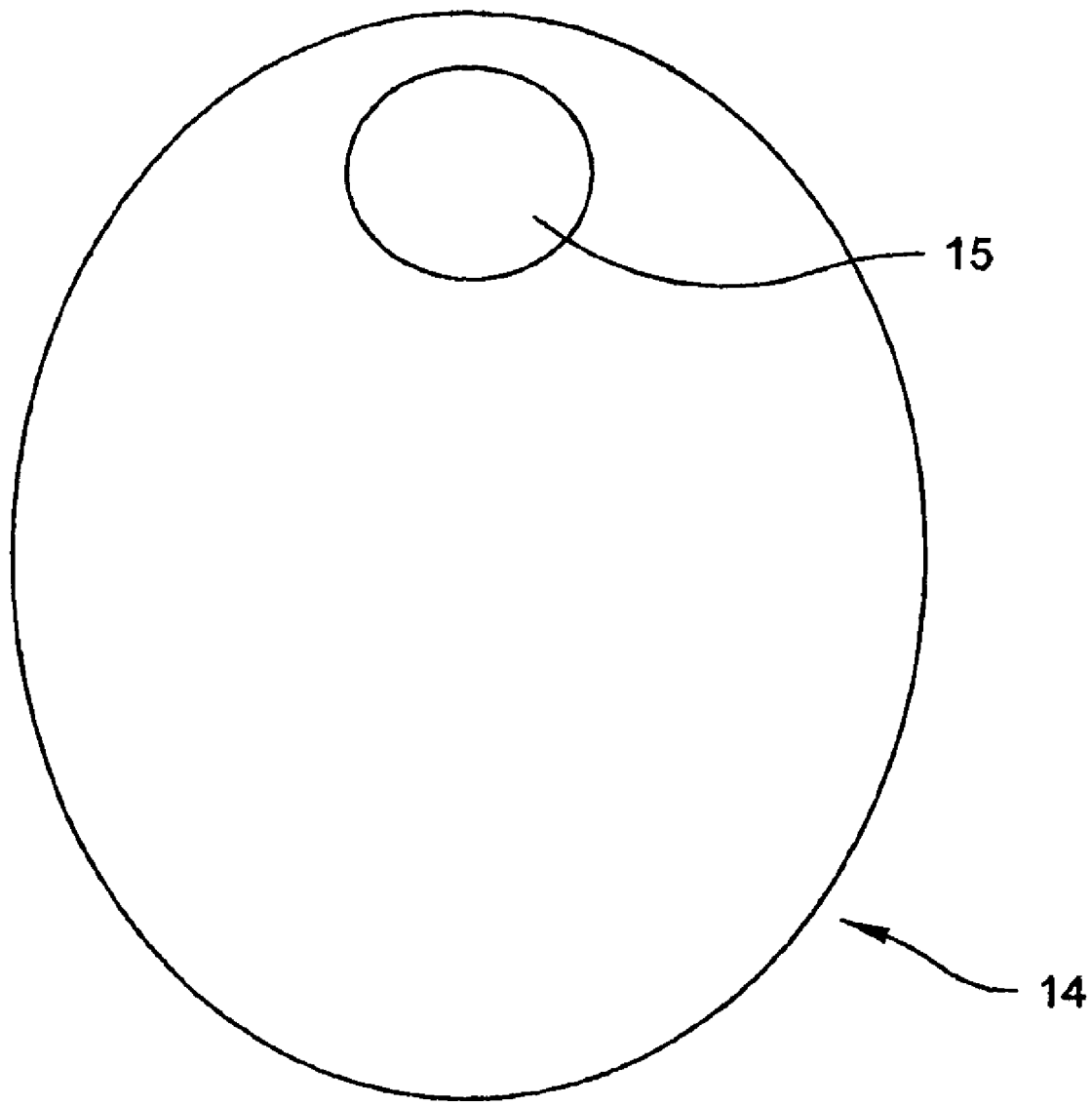
FIG. 3b is a frontal elevation view of an alternate embodiment having a substantially elliptical shape.

Referring now to FIG. 3b, an alternate embodiment of the therapeutic pad 14 is shown wherein upper and lower thermal elements 18, 19 or lower thermal element 19 alone comprising a structure having a substantially elliptical shape.

Referring again to FIG. 3a, upper thermal element 18 and lower thermal element 19 meet along a fold 16 along the minor axis 37 of the therapeutic pad 14. While it is preferred to have the portal 15 along the center of the major axis 36 of the therapeutic pad 14 and disposed between the upper thermal element 18 and lower thermal element 19, it is also possible for the portal 15 to be located along either the upper thermal element 18 or the lower thermal element 19. An optional pair of lift tabs 17a-17b is shown along one edge of the upper thermal element 18; however, other arrangements and locations are possible.

Figure 4:
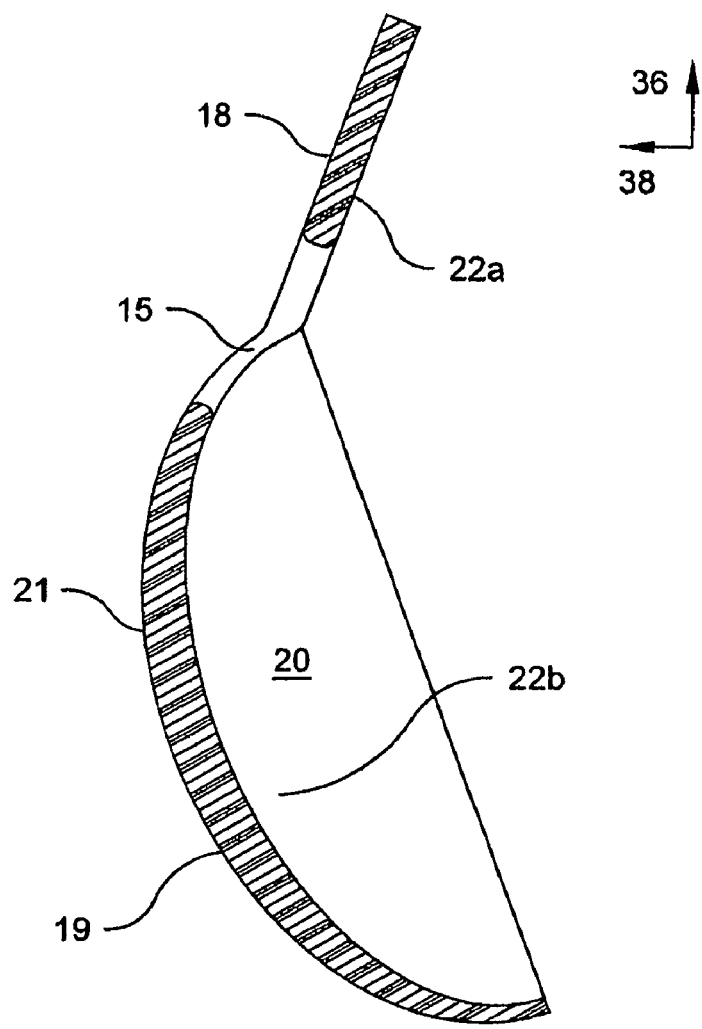
FIG. 4 is a sectional view from FIG. 3a along the major axis of the present invention showing cup-shaped structure of the lower heating element and generally planar structure of the upper heating element.
Figure 5:
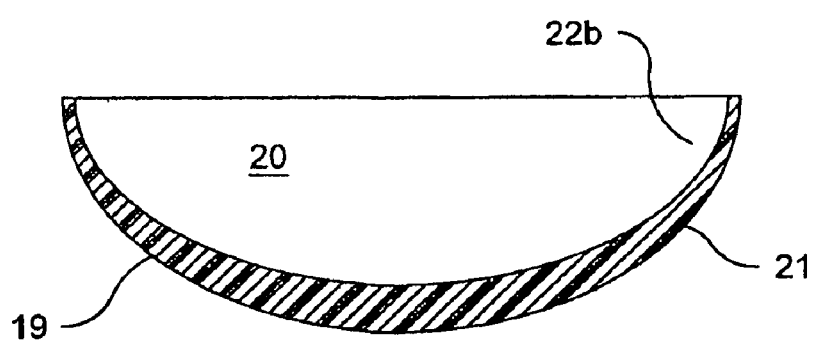
FIG. 5 is a sectional view from FIG. 3a along a minor axis of the present invention showing the cup-shaped structure of the lower heating element.

Referring now to FIGS. 4 and 5, cross sectional views of one embodiment of the present invention along the major axis 36 and minor axis 38, respectively, are shown with a generally planar profile for the upper thermal element 18 and a cup-shaped profile for the lower thermal element 19. The upper thermal element 18 is intended to contact upper portions of the groin which could include the abdominal wall. The planar shape of the upper thermal element 18 also might include a slight curvature along one or both axes, so as to better match the contour of the groin. The combined profiles along the upper thermal element 18 and lower thermal element 19 form a contact surface 22a-22b approximating surface features of the groin and genitalia.

When used by a male, the lower thermal element 19 is intended to contact the groin, including penis 3 and scrotum 6, in a conformal fashion. The lower thermal element 19 is provided with substantial curvature along its major axis 36 and its minor axis 38, as represented in FIGS. 4 and 5, respectively. The described compound curvature forms a support region 20 of sufficient volume to contact, hold and support the genitalia. The portal 15 is aligned with the urethra to allow for the passage of urine.

When used by a female, the lower thermal element 19 is intended to contact the groin in a conformal fashion. The therapeutic pad 14 would have curvature similar to that along the major axis 36 shown in FIG. 4 and less curvature along its minor axis 38. The portal 15 is aligned with the urethra to allow for the passage of urine.

Referring again to FIGS. 4 and 5, the therapeutic pad 14 may be composed of one or more materials of uniform thickness, as shown along the upper thermal element 18, or a tapered thickness profile, as shown along the lower thermal element 19. As mentioned above, the portal 15 completely traverses the thickness of the therapeutic pad 14 from contact surface 22a-22b to exterior surface 21. The portal 15 allows urine to pass from the urinary tract of the user to a receptacle. Male applications require the portal 15 to be sufficiently large and circular, so as to allow insertion of the penis 3 through the therapeutic pad 14. It is preferred for the sides of the portal 15 to contact the penis 3, so as to communicate heat to the base of the penis 3.

Figure 6:
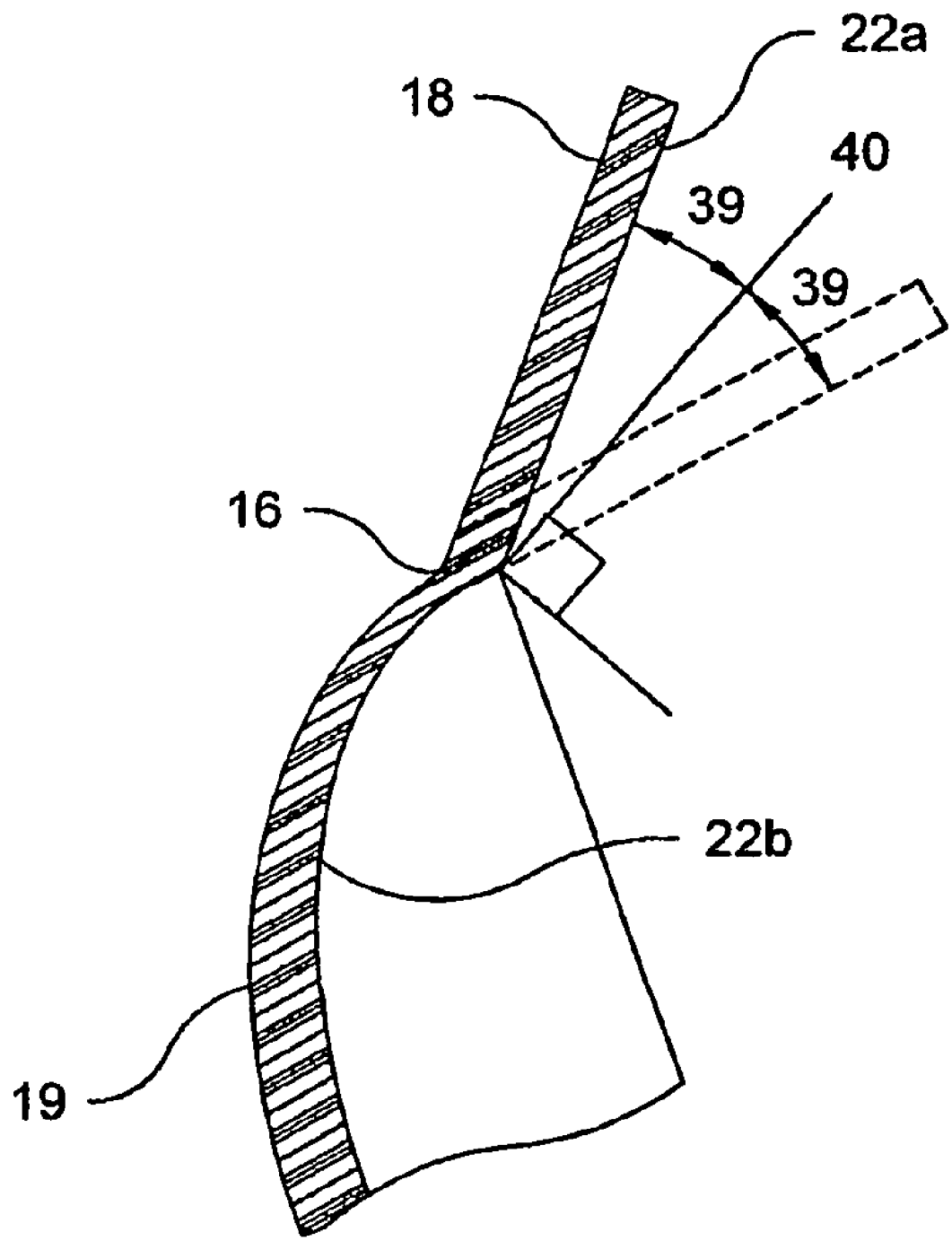
FIG. 6 is a partial section view from FIG. 3a showing the seam between upper and lower heating elements and angular orientation between the elements.

Upper thermal element 18 and lower thermal element 19 may be comprised of a single element or two or more elements molded, formed, or otherwise joined together via fabrication methods understood in the art. Referring now to FIG. 6, contact between upper and lower thermal elements 18, 19 is provided along a fold 16. The fold 16 may allow flexure between upper and lower thermal elements 18, 19 during use, so as to further conform the therapeutic pad 14 to the groin.

The upper thermal element 18 is disposed in an angular fashion with respect to the lower thermal element 19, herein identified as the offset angle 39. The offset angle 39 is defined as the angle between a projection 40 tangentially aligned with the contact surface 22b of the lower thermal element 19, where it contacts the upper thermal element 18, and the contact surface 22a of the upper thermal element 18. While the offset angle 39 may include a broad range of values, values less than 90 degrees are preferred.

Figure 7:
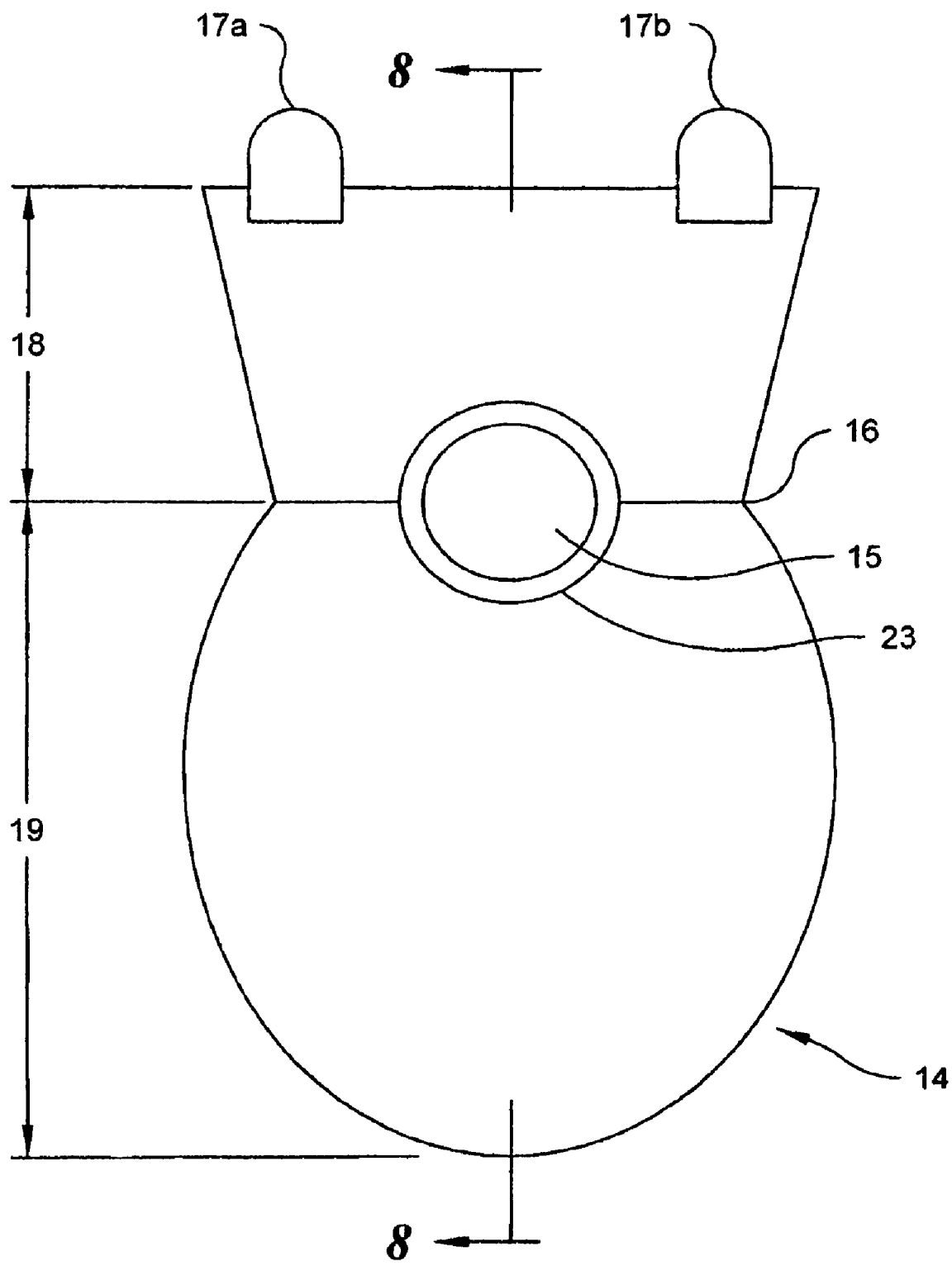
FIG. 7 is a frontal elevation view of an alternate embodiment of the present invention showing a sleeve about the portal.

Referring now to FIG. 7, an alternate embodiment of the therapeutic pad 14 from FIG. 3 is shown having an optional portal sleeve 23. The portal sleeve 23 is a substantially cylindrical structure composed of a thermally heatable material identical or similar to that comprising the upper and lower thermal elements 18, 19. The portal sleeve 23 is advantageous to communicate heat along the penis 3.

Figure 8:
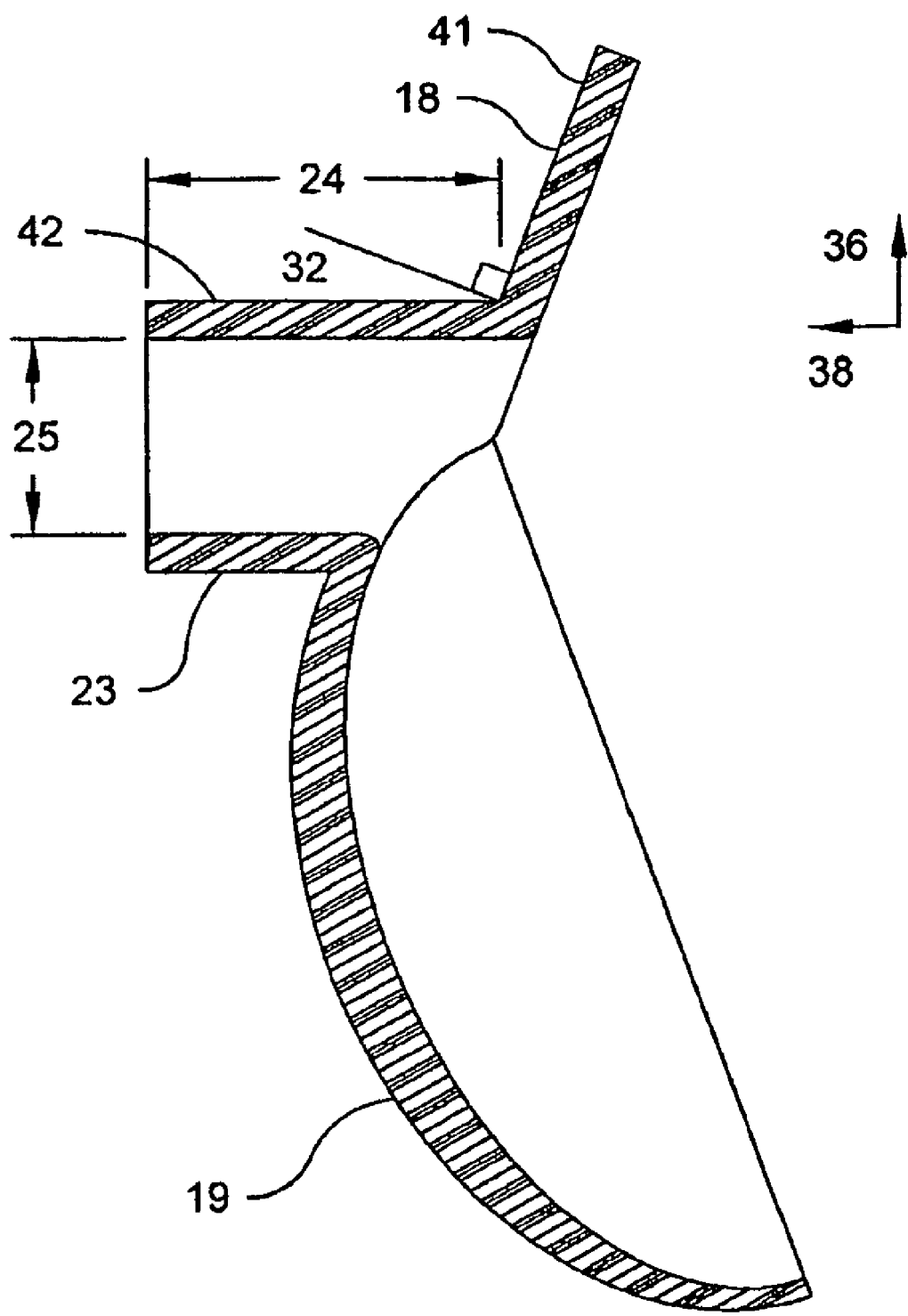
FIG. 8 is a sectional view from FIG. 7 along the major axis of the present invention showing the portal sleeve projecting from the upper and lower heating elements in a bisecting arrangement at an angle and width subject to anatomical requirements.

Referring now to FIG. 8, the portal sleeve 23 is shown as a linear cylinder projecting outward from the upper and lower thermal elements 18, 19. It is likewise possible for the portal sleeve 23 to have curvature along its length 24 in a particular direction. A variety of lengths 24 and diameters 25 are possible for the portal sleeve 23. For example, the length 24 of the portal sleeve 23 may be less than that of the penis 3 so as to extend from the portal sleeve 23. It is also possible for the portal sleeve 23 to be longer than the penis 3 so that the head of the penis 3 resides within the portal sleeve 23 and is heated thereby. The diameter 25 of the portal sleeve 23 should allow for insertion of the penis 3 in an unimpeded fashion. It is preferred that the diameter 25 be at least as large as that of the penis 3. Where the diameter 25 is greater than that of the penis 3, the user may prefer to pinch or otherwise grasp and squeeze the portal sleeve 23 to ensure contact between portal sleeve 23 and penis 3.

The portal sleeve 23 is molded, formed or joined in a fixed fashion via methods understood in the art or otherwise contacting in a removable fashion to the upper and lower thermal elements 18, 19. In the latter, the portal sleeve 23 is positioned over the penis 3 independent of the upper and lower thermal elements 18, 19.

Referring again to FIG. 8, the portal sleeve 23 is oriented in an angular fashion with respect to the upper thermal element 18. The declination angle 32 is defined as the angle between a normal line from the exterior surface 41 along the upper thermal element 18 and the exterior surface 42 along the portal sleeve 23 along a plane through the center of the major axis 36. The declination angle 32 may include a range of values from zero, so that the portal sleeve 23 is perpendicular to the upper thermal element 18, or greater than zero, so that the penis 3 is angled downward towards the scrotum 6.

Figure 9A:
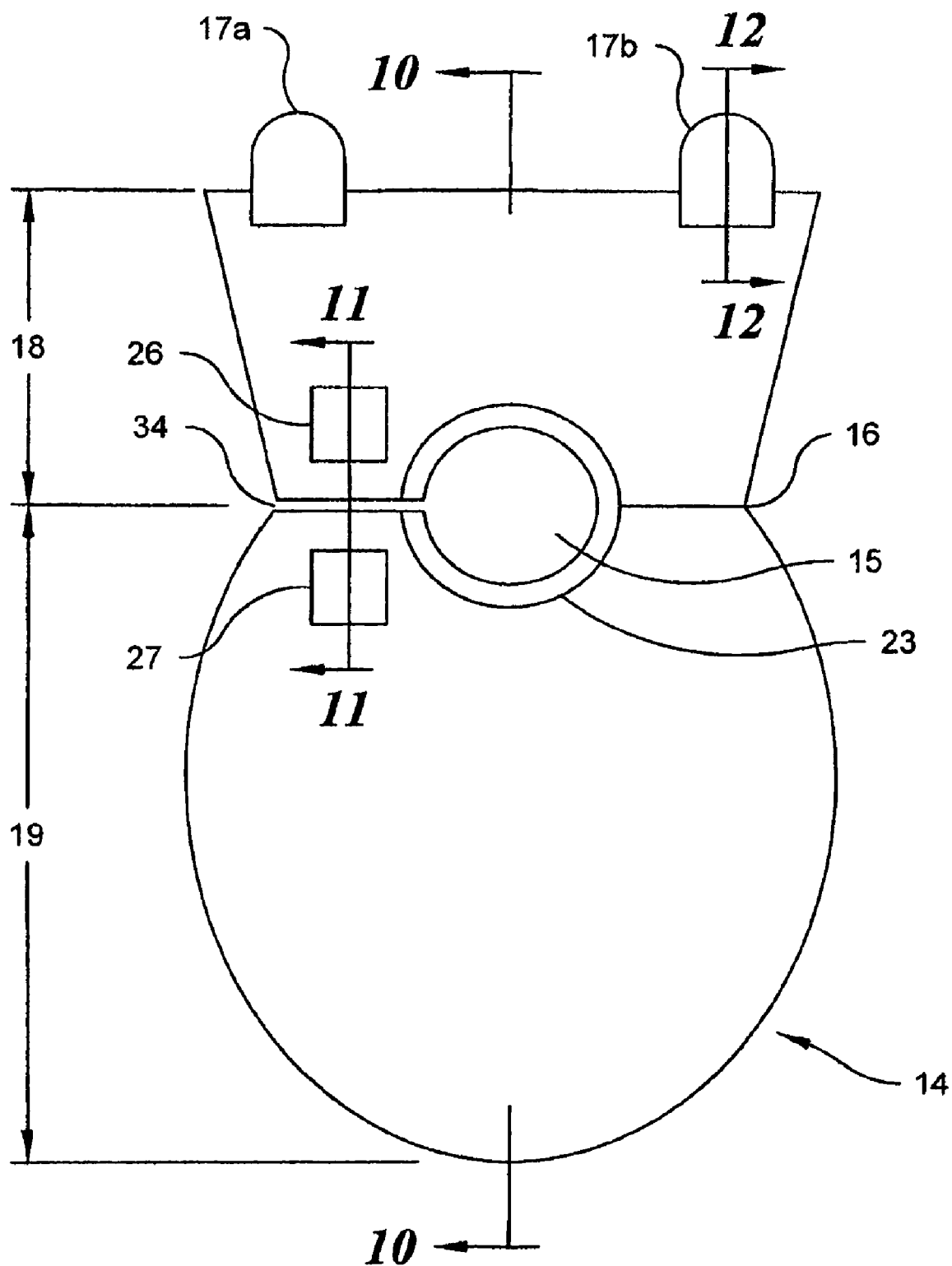
FIG. 9a is a frontal view of another alternate embodiment of the present invention showing a horizontally disposed slit along one side between upper and lower heating elements and portal sleeve.
Figure 9B:
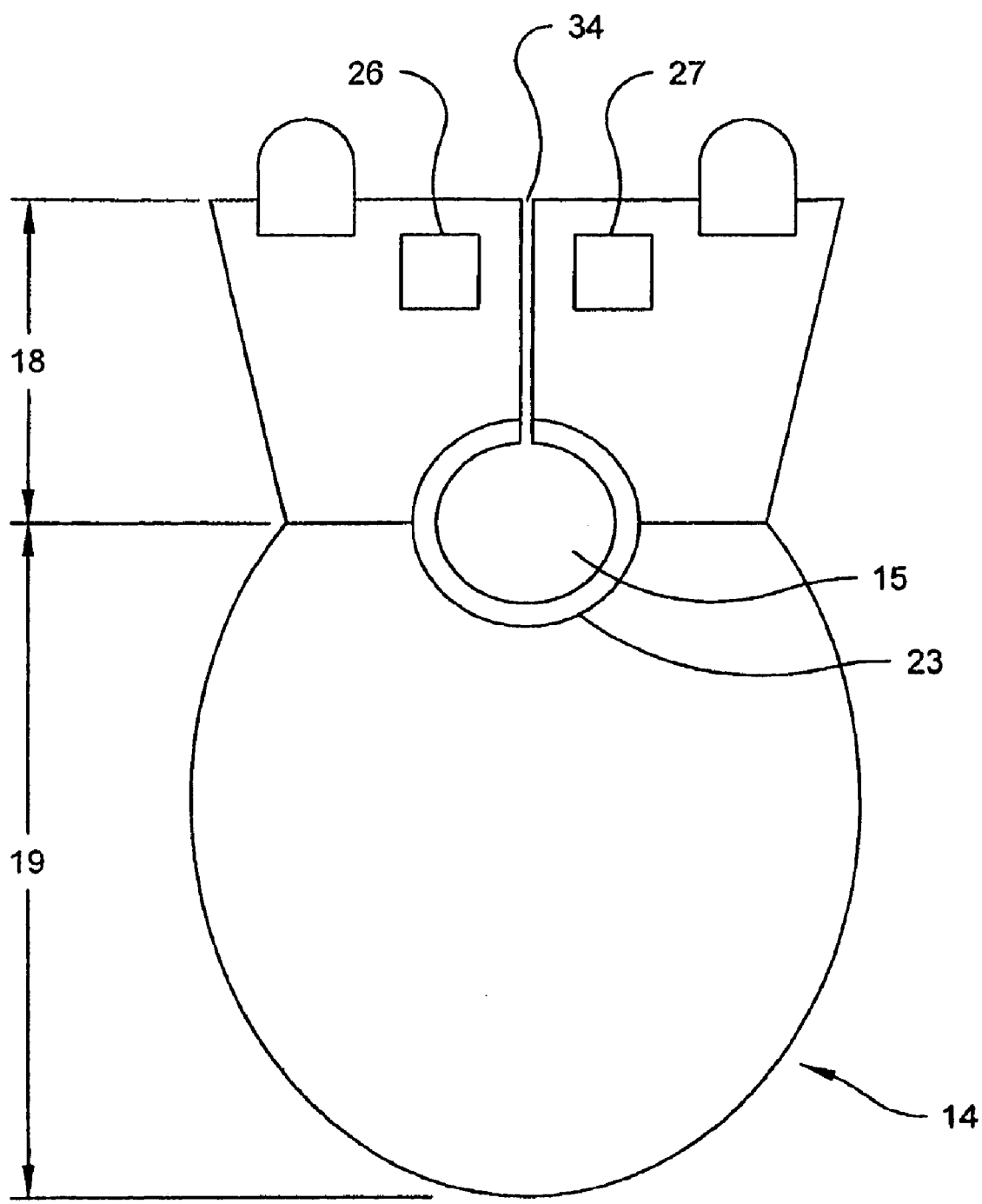
FIG. 9b is a frontal view of another alternate embodiment showing a vertically disposed slit through upper heating element and portal sleeve.
Figure 10:
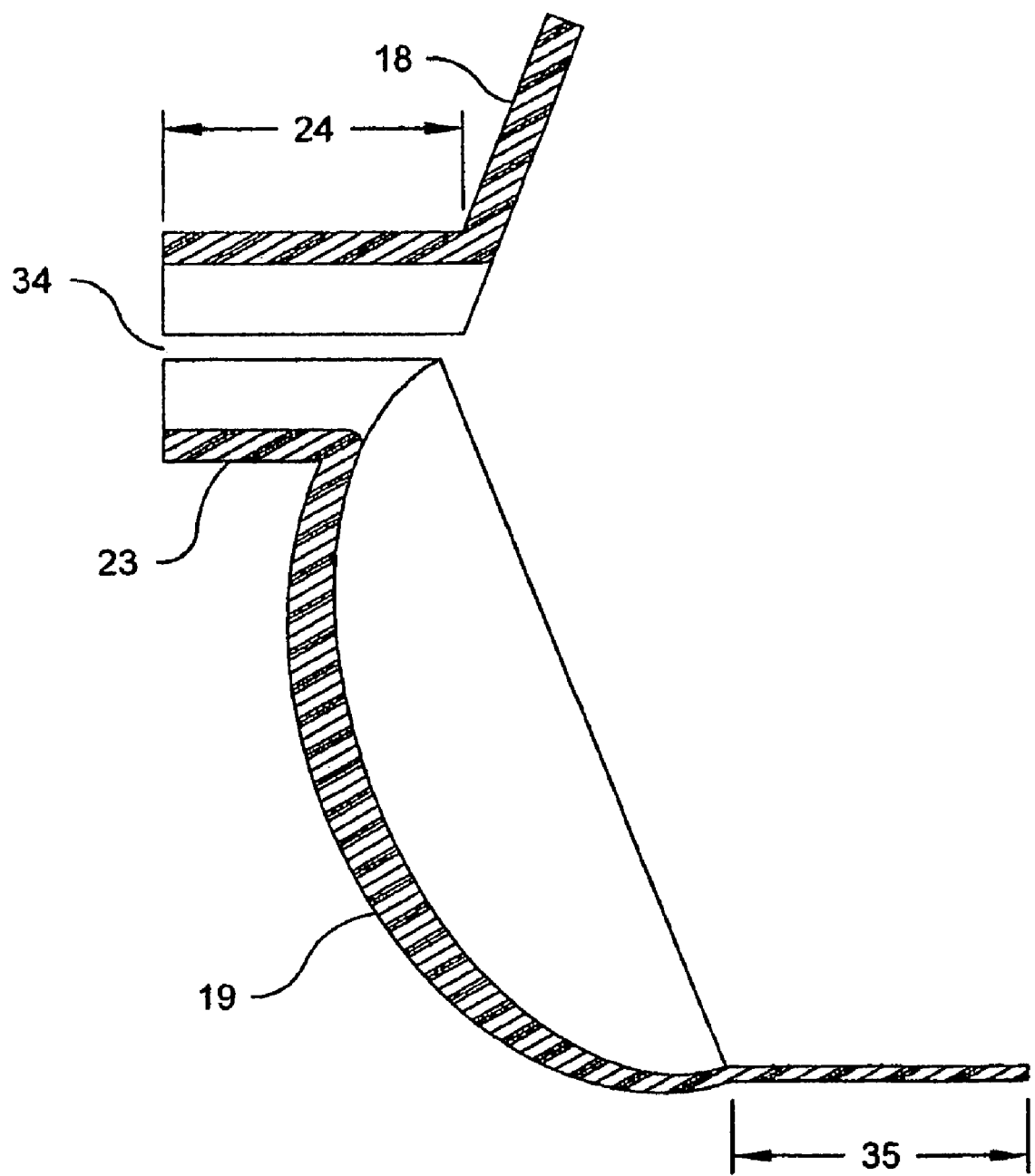
FIG. 10 is a sectional view from FIG. 9a along the major axis of the present invention showing the slit along the length of the portal sleeve and an optional extension element projecting from the bottom edge of the lower thermal element.

Referring now to FIGS. 9a and 10, an alternate embodiment of the therapeutic pad 14 in FIG. 7 is shown with an optional slit 34, first ring 26, and second ring 27. The slit 34 is shown traversing one side of the present invention along the fold 16 and along the length 24 of the portal sleeve 23. The slit 34 may be introduced during manufacture of the therapeutic pad 14 or mechanically cut into the therapeutic pad 14 after manufacture. The primary purpose of the slit 34 is to allow for the opening and widening of the portal 15 to ease insertion of the penis 3. It is likewise possible for the slit 34 to be oriented vertically, as shown in FIG. 9b, or at some angle between horizontal and vertical.

Figure 11:
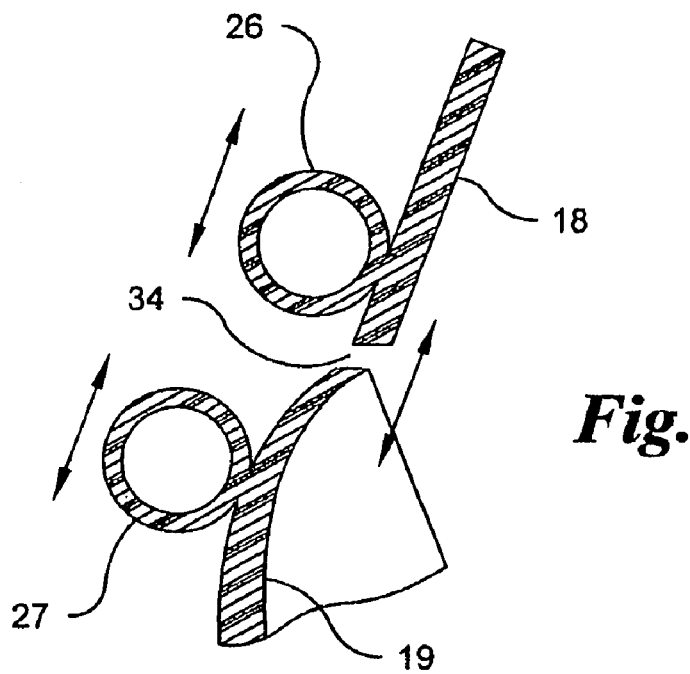
FIG. 11 is an enlarged sectional view from FIG. 9a showing a first ring attached to the upper heating element and second ring attached to the lower heating heat about the slit.

Referring now to FIG. 11, first ring 26 and second ring 27 are shown disposed about the slit 34. While a variety of attachment schemes are possible, first ring 26 and second ring 27 may be either mechanically or adhesively fastened to the upper thermal element 18 and lower thermal element 19, respectively.

First and second rings 26, 27 are cylindrical structures or the like composed of a thermally resistant material, preferably a polymer, one example being polyethylene. First and second rings 26, 27 should be sufficiently large so as to allow insertion of a finger or thumb. It is preferred that first and second rings 26, 27 be aligned with the slit 34 so that finger and thumb are substantially parallel to the slit 34 when residing within the first and second rings 26, 27. The primary purpose of the first and second rings 26, 27 is to enable the user to control opening and closing of the slit 34 via movement of the upper and lower thermal elements 18, 19 for positioning of the therapeutic pad 14 over the penis 3 and subsequent use. However, first and second rings 26, 27 may be employed with or without other optional elements described herein.

Referring again to FIG. 10, an optional extension element 35 is shown attached to the lower thermal element 19 opposite of the upper thermal element 18. The extension element 35 is a generally planar structure composed of a thermally heatable material identical or similar to that comprising the upper and lower thermal elements 18, 19. The length and angular placement of the extension element 35 should be sufficient to ensure contact with tissue along and/or adjacent to the perineum 7. The width of the extension element 35 should allow it to be grasped and compressed between the legs of the user. The extension element 35 is advantageous to communicate heat to regions beyond the scrotum 6 including the perineum 7.

Figure 12:
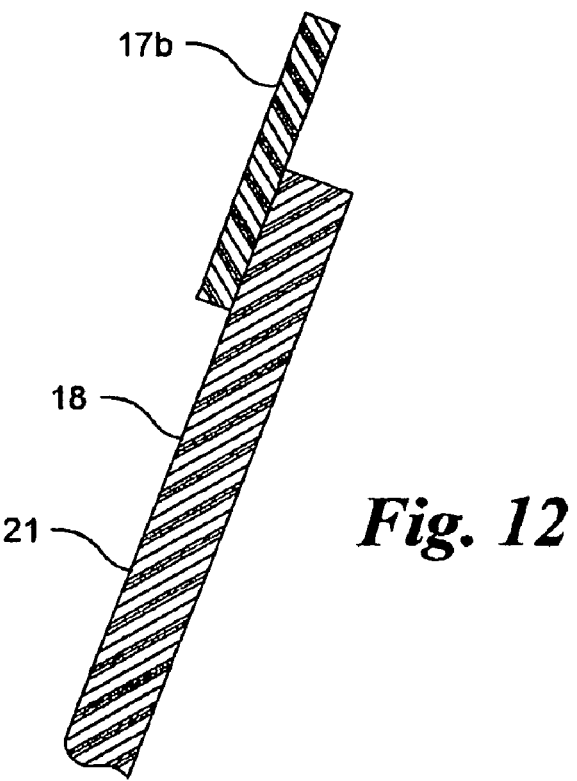
FIG. 12 is an enlarged sectional view from FIG. 9a showing attachment of the lift tab to the exterior surface of the upper heating element.

Referring now to FIG. 12, an optional lift tab 17b is shown contacting and attached to the exterior surface 21 of the upper thermal element 18. While a variety of attachment schemes are possible, upper lift tabs 17a-17b may be mechanically or adhesively fastened to the upper thermal element 18 and/or lower thermal element 19. It is likewise possible for lift tabs 17a-17b to be embedded within and projecting from the therapeutic pad 14. Each lift tab 17a-17b is a substantially planar structure or the like composed of a thermally resistant material, preferably a polymer, one example being polyethylene. Lift tabs 17a-17b should have sufficient area so as to allow the user to grasp the lift tab 17a or 17b between thumb and index finger without contacting heated regions of the therapeutic pad 14. The primary purpose of the lift tabs 17a-17b is to facilitate retrieval from a hydrocollator or microwave oven after a heating cycle. Lift tabs 17a-17b may be employed with or without other optional elements described herein.

Figure 13:
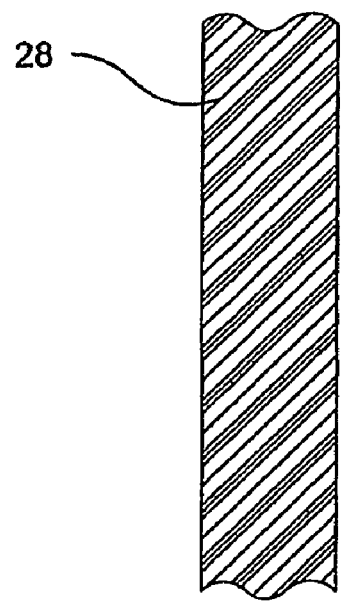
FIG. 13 is an enlarged section view of an exemplary construction of the pad wall.

Referring now to FIG. 13, an enlarged sectional view of the pad wall 28 is shown for one embodiment of the present invention and representative of the structure composing the upper thermal element 18, lower thermal element 19, portal sleeve 23, and extension element 35. The pad wall 28 may composed of materials externally heated via a hydrocollator, microwave oven or the like or materials internally heated via a chemical reaction or resistive heating elements. It is generally preferred that the pad wall 28 retains the original shape of the therapeutic pad 14 during heating and cooling, yet remain sufficiently pliable to conform to the groin and regions adjacent thereto.

A variety of materials known within the medical arts for applying heat to portions of a human body are applicable to the present invention. In the present invention, the therapeutic pad 14 should be heatable to a temperature exceeding 94.6 degrees Fahrenheit, preferably from 95 to 110 degrees Fahrenheit. The pad wall 28 should be thermally retentive to communicate heat within the target temperature range to the groin and surrounding tissues until urinary function is initiated, typically at least 10 seconds.

Externally heated materials may include commercially known items including silicone gel, polyurethane gels, hydrogels, and the like. For example, hydrogel materials are described in U.S. Pat. Nos. 4,671,267, 4,243,041, 4,092,982, and 4,055,188, and sold as wraps under the trademark ELASTOGEL by Southwest Technologies, Inc. of Kansas City, Mo. Hydrogel compositions include, but are not limited to, a gel including a water soluble humectant, examples being glycerin, ethylene glycol, propylene glycol, dimethyl sulfoxide and dimethyl formamide, entrapped within a matrix composed of polymers, copolymers, or terpolymers. Gels are known to maintain pliability over a relatively broad temperature range and capable of absorbing and desorbing moisture.

In yet another example, internally heated materials may include wraps and packs having a composition therein that exhibits a chemical reaction that is exothermic. Compositions and packs described in U.S. Pat. Nos. 6,393,843 and 4,067,313 are exemplary of materials applicable to the present invention. One specific non-limiting family of compositions consists of anhydrous calcium chloride, anhydrous sodium acetate, and calcium oxide which produce an exothermic reaction when mixed with water.

Figure 14:
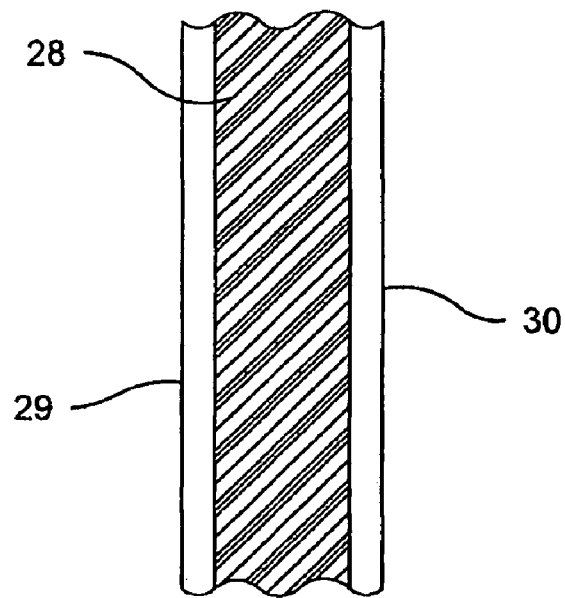
FIG. 14 is an enlarged section view of an exemplary pad wall with exterior and interior covers.

In some applications, it might be advantageous to apply moisture to the groin. Referring now to FIG. 14, an exemplary embodiment is shown have an exterior cover 29 and interior cover 30 contacting and otherwise attached to the pad wall 28. While a variety of such covering are known within the art, moisture and heat permeable stretchable clothes are preferred.

In yet other embodiments, it might be advantageous to provide a structure within the pad wall 28 to generally maintain the shape of the therapeutic pad 14, improve its shape retention properties at elevated temperatures, and improve its pliability and shape retention during use.

Figure 15:
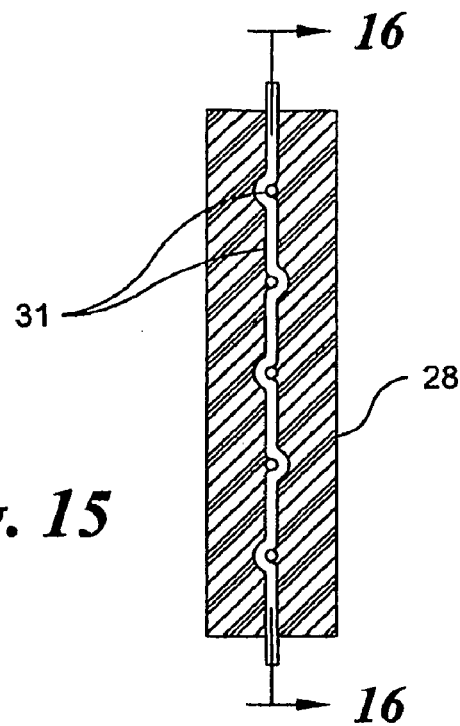
FIG. 15 is an enlarged section view of an alternate embodiment of the pad wall having support elements therein.
Figure 16:
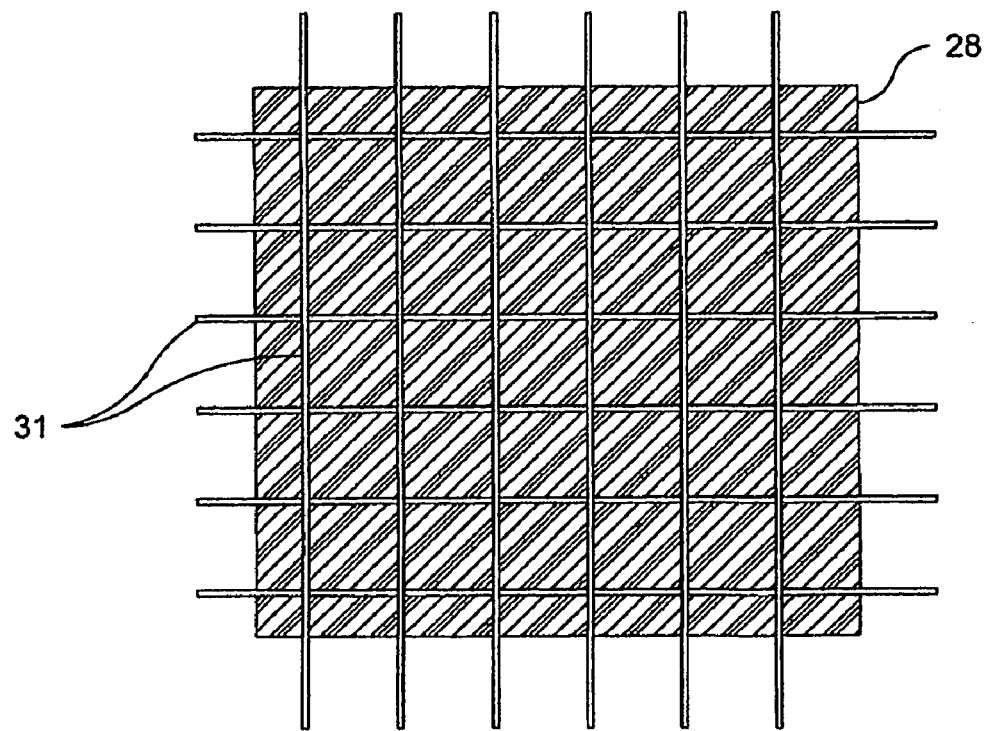
FIG. 16 is a sectional view from FIG. 15 showing an exemplary two-dimensional mesh structure composed of a plurality of support elements.

Referring now to FIGS. 15-16, an exemplary embodiment is shown have a plurality of optional support elements 31 embedded within the pad wall 28. It is likewise possible, for the support elements 31 to be attached or otherwise embedded along one or more surfaces of the pad wall 28. Support elements 31 may include a wide variety of plastics, metals, and plastic coated metals having a substantially strip-like or wire shape. Support elements 31 are preferred to be pliable and capable of retaining a shape after being deformed. It is likewise possible for the support elements 31 to also be composed of resistive wire heating elements known within the art, which may be electrically connected to an AC or DC power source to heat the pad wall 28.

Figure 17:
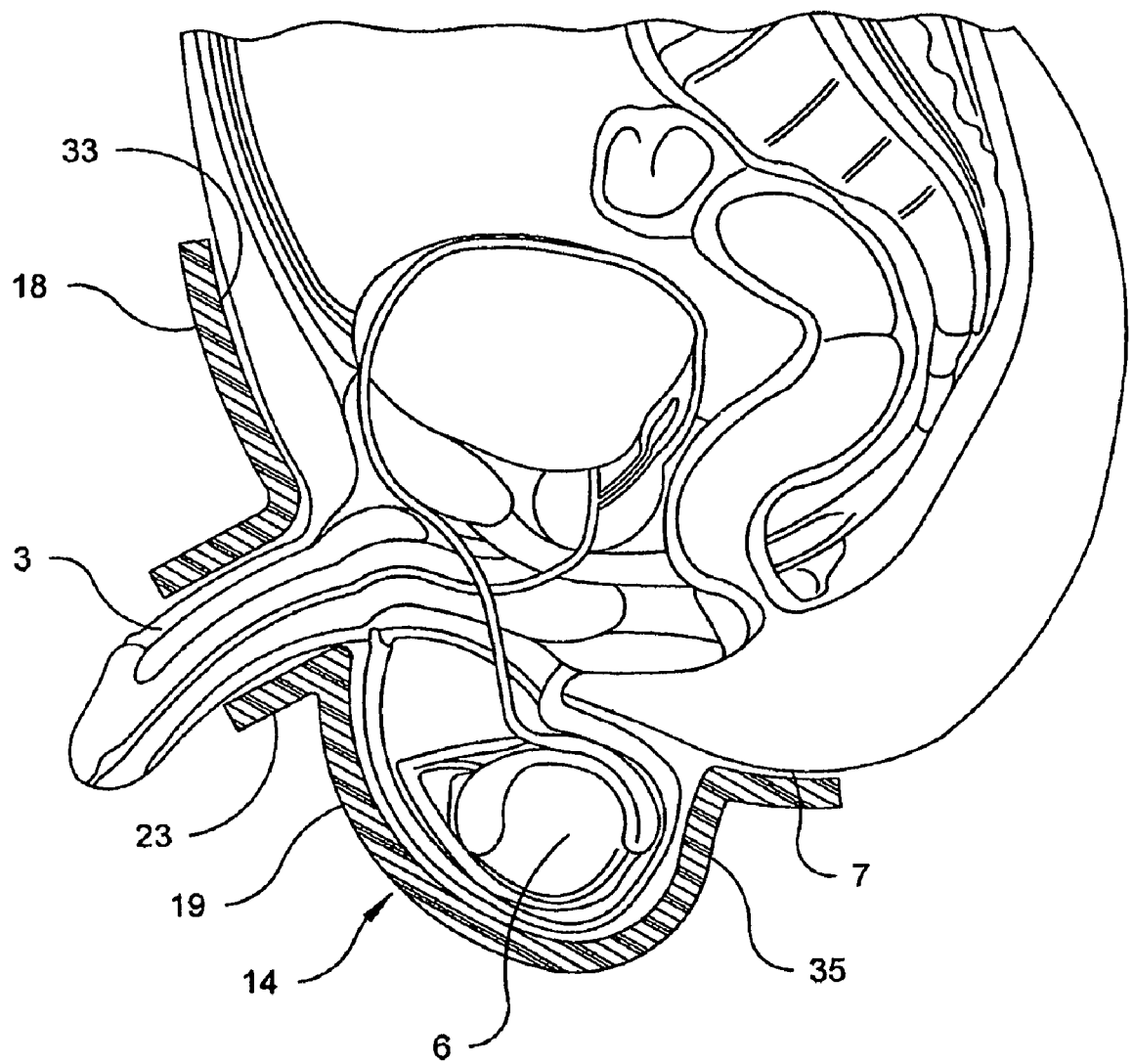
FIG. 17 is a functional schematic in the form of a sectional view showing contact between abdominal wall and upper heating element, penis and portal sleeve, scrotum and lower heating element, and extension element and tissue adjacent to the perineum.

Referring now to FIG. 17, an exemplary therapeutic pad 14 is shown contacting the abdominal wall 33, penis 3, scrotum 6, and perineum 7 of a male subject. In application, the user positions the therapeutic pad 14 so that the upper thermal element 18 contacts the abdominal wall 33, lower thermal element 19 contacts the scrotum 6, portal sleeve 23 contacts the penis 3, and extension element 35 contacts the perineum 7. The therapeutic pad 14 might be positioned with both hands and thereafter held in place with one hand while the penis 3 is grasped and aimed with the other hand.

Application and use of the therapeutic pad 14 requires it to be heated. For externally heated embodiments, the therapeutic pad 14 is placed into a commercially available hydrcollotar or microwave oven to heat the pad wall 28 to the desired temperature. In microwave applications, it might be desired to wet the therapeutic pad 14 prior to heating so as to apply moist heat to targeted areas. Thereafter, the therapeutic pad 14 is removed from the hydrocollator or microwave oven via the lift tabs 17a-17b and applied onto the groin so as to communicate heat to the groin, genitals, perineum and/or abdomen, thereby initiating urinary function.

For internally heated embodiments, the chemical reaction is initiated within the therapeutic pad 14 via mixture of two or more components so as to heat the pad wall 28 to the desired temperature. Electrically induced heating requires the support elements 31 to be energized via electrical circuitry understood in the art including connectivity with a power outlet or batteries. Again, it might be desired to wet the therapeutic pad 14 prior to heating so as to apply moist heat to targeted areas. Thereafter, the therapeutic pad 14 is applied onto the groin so as to communicate heat to the groin, genitals, perineum and/ or abdomen, thereby initiating urinary function.

As is evident from the explanation above, the described invention is capable of thermally stimulating the pudendal nerve which is understood to induce urination directly or indirectly via the inferior rectal nerve, perineal nerve, posterior scrotal nerves, and/or dorsal nerve.

Accordingly, the described invention is expected to be used by individuals unable to urinate because of an enlarged prostate, nervousness, or lack of present urge. The invention is applicable to medical facilities, sports teams, employers, law enforcement, and the like to induce urination "on-the spot" for the purpose of collecting samples for medical tests and drug screening. The present invention is applicable to males and females, although use by the latter group is unrelated to the prostate related problems discussed herein.

The description above indicates that a great degree of flexibility is offered in terms of the present invention. Although the present invention has been described in considerable detail with reference to certain preferred versions thereof, other versions are possible. Therefore, the spirit and scope of the appended claims should not be limited to the description of the preferred versions contained herein.

What is claimed is:

1. A therapeutic device for thermally assisted urinary function comprising:

(a) a pad configured to conformably contact a groin, said pad composed of a first heatable material, said pad having a portal disposable about an urethra;

(b) a slit partially bisecting said pad; and (c) a pair of rings disposed about said slit and attached to said pad for opening and closing said slit.

2. The therapeutic device for thermally assisted urinary function of claim 1, further comprising:

(d) at least one lift tab disposed along an edge of said pad.

3. The therapeutic device for thermally assisted urinary function of claim 1, further comprising:

(d) an extension element attached to said pad to conformably contact at least one region adjacent to and behind said groin, said extension element composed of a second heatable material.

4. The therapeutic device for thermally assisted urinary function of claim 3, further comprising:

(e) at least one lift tab disposed along an edge of said pad.

5. The therapeutic device for thermally assisted urinary function of claim 1, further comprising:

(d) a portal sleeve disposed about said portal and projecting outward there from, said portal sleeve composed of a second heatable material, said slit partially bisects said portal sleeve.

6. The therapeutic device for thermally assisted urinary function of claim 5, further comprising:

(e) at least one lift tab disposed along an edge of said pad.

7. The therapeutic device for thermally assisted urinary function of claim 5, further comprising:

(e) an extension element attached to said pad to conformably contact at least one region adjacent to and behind said groin, said extension element composed of a third heatable material.

8. The therapeutic device for thermally assisted urinary function of claim 1, further comprising:

(d) a moisture retentive cover about said therapeutic device.

9. The therapeutic device for thermally assisted urinary function of claim 1, further comprising:

(d) at least one support element along said therapeutic device.

10. The therapeutic device for thermally assisted urinary function of claim 9, further comprising:

(e) a moisture retentive cover about said therapeutic device.

11. The therapeutic device for thermally assisted urinary function of claim 9, wherein said at least one support element is a resistive heating element.

12. The therapeutic device for thermally assisted urinary function of claim 1, wherein said first heatable material is a silicone gel, a polyurethane gel, or a hydrogel.

13. The therapeutic device for thermally assisted urinary function of claim 1, wherein said first heatable material is composed of a composition capable of producing an exothermic reaction.

14. A method for thermally assisted urinary function comprising the steps of:

(a) heating a therapeutic device comprising:

(i) a pad configured to conformably contact a groin, said pad composed of a first heatable material and having a portal disposable about an urethra;

(ii) a slit partially bisecting said pad; and (iii) a pair of rings disposed about said slit and attached to said pad for opening and closing said slit;

(b) applying said therapeutic device to cover and contact said groin;

(c) communicating heat from said therapeutic device to said groin; and
(d) initiating urination.

15. The method for thermally assisted urinary function of claim 14, further comprising the step of:
(e) communicating heat from said therapeutic device to a penis via a portal sleeve composed of a second heatable material disposed about said portal and projecting outward there from, said slit partially bisects said portal sleeve.

16. The method for thermally assisted urinary function of claim 14, further comprising the step of:
(e) communicating heat from said therapeutic device to at least one region adjacent to and behind said groin via an extension element composed of a second heatable material attached to said pad.

17. The method for thermally assisted urinary function of claim 16, further comprising the step of:
(f) communicating heat from said therapeutic device to a penis via a portal sleeve composed of a third heatable material disposed about said portal and projecting outward there from, said slit partially bisects said portal sleeve.

18. The method for thermally assisted urinary function of claim 14, further comprising the step of:
(e) removing said therapeutic device prior to onset of urination.

19. The method for thermally assisted urinary function of claim 14, further comprising the step of:
(e) removing said therapeutic device during urination.

20. The method for thermally assisted urinary function of claim 14, further comprising the step of:
(e) removing said therapeutic device after urination is completed.

* * * * *